United States Patent
Hirooka (10) Patent No.: US 10,371,675 B2
(45) Date of Patent: Aug. 6, 2019

(54) DATA PROCESSING DEVICE FOR COMPREHENSIVE TWO-DIMENSIONAL CHROMATOGRAPH

(71) Applicant: SHIMADZU CORPORATION, Kyoto-shi, Kyoto (JP)

(72) Inventor: Megumi Hirooka, Uji (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 15/321,027

(22) PCT Filed: Jun. 24, 2014

(86) PCT No.: PCT/JP2014/066625
§ 371 (c)(1),
(2) Date: Dec. 21, 2016

(87) PCT Pub. No.: WO2015/198385
PCT Pub. Date: Dec. 30, 2015

(65) Prior Publication Data
US 2017/0160245 A1   Jun. 8, 2017

(51) Int. Cl.
*G01N 30/46* (2006.01)
*G01N 30/86* (2006.01)

(52) U.S. Cl.
CPC .......... *G01N 30/46* (2013.01); *G01N 30/463* (2013.01); *G01N 30/861* (2013.01); *G01N 30/8651* (2013.01); *G01N 30/8679* (2013.01)

(58) Field of Classification Search
None
See application file for complete search history.

(56) References Cited

U.S. PATENT DOCUMENTS

| | | | |
|---|---|---|---|
| 6,576,472 B1* | 6/2003 | Geysen | C40B 50/10 436/161 |
| 2014/0260536 A1* | 9/2014 | Sadowski | G01N 30/8675 73/23.37 |
| 2017/0336370 A1* | 11/2017 | Noda | G01N 30/8675 |

FOREIGN PATENT DOCUMENTS

JP   2011-122822 A   6/2011

OTHER PUBLICATIONS

Hope P. Bailey, Chemometric Resolution and Quantification of Four-Way Data Arising from Comprehensive 2D-LC-DAD Analysis of Human Urine, Chemometr Intell Lab Syst. Author manuscript; Published in final edited form as: Chemometr Intell Lab Syst. Mar. 15, 2011, p. 1-26). https://www.ncbi.nlm.nih.gov/pmc/articles/PMC3762254/pdf/nihms227355.pdf.*

(Continued)

*Primary Examiner* — Tung S Lau
(74) *Attorney, Agent, or Firm* — Sughrue Mion, PLLC (57) ABSTRACT

A two-dimensional chromatogram creator creates a two-dimensional chromatogram based on data obtained for each of two samples. A chromatogram difference calculator creates a two-dimensional differential chromatogram showing the intensity difference between the two two-dimensional chromatograms. A blob detector detects blobs on each chromatogram. A matching-blob extractor compares the blobs located on the differential chromatogram with those located on each of the two other chromatograms, to extract blobs which can be considered to be located at the same temporal position. If there are two blobs extracted at the same temporal position on the two chromatograms, a normalized value of the intensity difference between the two blobs is calculated, and the line type of the boundary line for indicating the extracted blob on the display is chosen according to that value. Important blobs having significant (Continued)

intensity differences on the two chromatograms being compared can be automatically selected and presented to analysis operators.

8 Claims, 5 Drawing Sheets

(56) References Cited

OTHER PUBLICATIONS

Saer Samanipoura, Analyte quantification with comprehensive two-dimensional gaschromatography: Assessment of methods for baseline correction,peak delineation, and matrix effect elimination for real samples, Nov. 25, 2014, p. 123-139.*

Barrett J. Nehilla, A Stimuli-Responsive, Binary Reagent System for Rapid Isolation of Protein Biomarkers, Anal. Chem. 2016, 88, p. 10404-10410.*

"GC Image (GCxGC Edition) Users' Guide, Comparative Analysis and Visualization", [online], GC Image LLC (USA), [accessed on Dec. 16, 2016], the Internet <URL: http://www.gcimage.com/gcxgc/usersguide/comparisons.html>.

"GC Image (GCxGC Edition) Users' Guide, Comparative Analysis and Visualization", [online], GC Image LLC (USA), [accessed on Jun. 9, 2014], the Internet <URL: http://www.gcimage.com/gcxgc/usersguide/comparisons.html>.

Miyagawa, "Gasukuromatogurafi/Shitsuryoubunseki-Hou No Nouyaku Zanryuu Bunseki Eno Riyou (Sono 2)—Houkatsuteki Nijigen Gasukuromatogurafu-Shitsuryoubunsekikei (GCxGC-MS) No Nouyaku Zanryuu Bunseki Eno Tekiyou—(Use of Gas Chromatography/Mass Spectrometry for Pesticide Residue Analysis (Part 2)—Application of Comprehensive Two-Dimensional Gas Chromatograph-Mass Spectrometer (GCxGC-MS) in Pesticide Residue Analysis)", Japanese Journal of Pesticide Science, 2012, pp. 104-111, vol. 37, No. 1.

Stephen E. Reichenbach, "Comprehensive two dimensional gas chromatography, Chapter 4: Data Acquisition, Visualization, and Analysis", Elsevier B.V., 2009, pp. 77-106.

International Search Report of PCT/JP2014/066625, dated Oct. 7, 2014. [PCT/ISA/210].

Written Opinion for PCT/JP2014/066625 dated Oct. 7, 2014 [PCT/ISA/237].

* cited by examiner

Fig. 1

Fig. 3A  ONE-DIMENSIONAL CHROMATOGRAM

Fig. 3B  ORDER OF DATA SEQUENCE IN TWO-DIMENSIONAL CHROMATOGRAM

Fig. 3C  TWO-DIMENSIONAL CHROMATOGRAM

DATA PROCESSING DEVICE FOR COMPREHENSIVE TWO-DIMENSIONAL CHROMATOGRAPH

CROSS REFERENCE TO RELATED APPLICATIONS

This application is a National Stage of International Application No. PCT/JP2014/066625 filed Jun. 24, 2014, the contents of all of which are incorporated herein by reference in their entirety.

TECHNICAL FIELD

The present invention relates to a data processing device for a comprehensive two-dimensional chromatograph used for processing data collected with a comprehensive two-dimensional gas chromatograph (GC) or comprehensive two-dimensional liquid chromatograph (LC).

BACKGROUND ART

As one technique for the GC analysis, a technique called the "comprehensive two-dimensional GC" (which is also called "GC×GC") is commonly known (for example, see Patent Literature 1 and Non Patent Literature 1).

In the comprehensive two-dimensional GC, various components contained in a sample are initially separated with a column which is the first dimension (which is hereinafter called the "primary column"). The thereby eluted components are introduced into a modulator. The modulator repeats an operation including the steps of catching the introduced components at regular intervals of time (which is normally within a range from a few seconds to approximately one dozen seconds; this interval of time is normally called the "modulation time"), detaching those components with an extremely narrow time bandwidth, and introducing them into a column which is the second dimension (which is hereinafter called the "secondary column"). In general, the component separation in the primary column is performed under such a separation condition that the elution occurs at a rate approximately equal to or slightly lower than the rate in a commonly used GC. On the other hand, as compared to the primary column, the secondary column has a different polarity, shorter length and smaller inner diameter, with the component separation performed under such a condition that each elution will be completed within the modulation time. In this manner, in the comprehensive two-dimensional GC, a plurality of components which have not been separated by the primary column and whose peaks overlap each other can be separated in the secondary column, whereby the separation performance is dramatically improved as compared to normal GCs.

A similar technique to the comprehensive two-dimensional GC is also known in the field of liquid chromatographic analysis, i.e. the comprehensive two-dimensional LC or LC×LC, which uses two columns having different separation characteristics. In the present description, both the comprehensive two-dimensional GC and the comprehensive two-dimensional LC are collectively called the "comprehensive two-dimensional chromatograph".

Figure 3A:
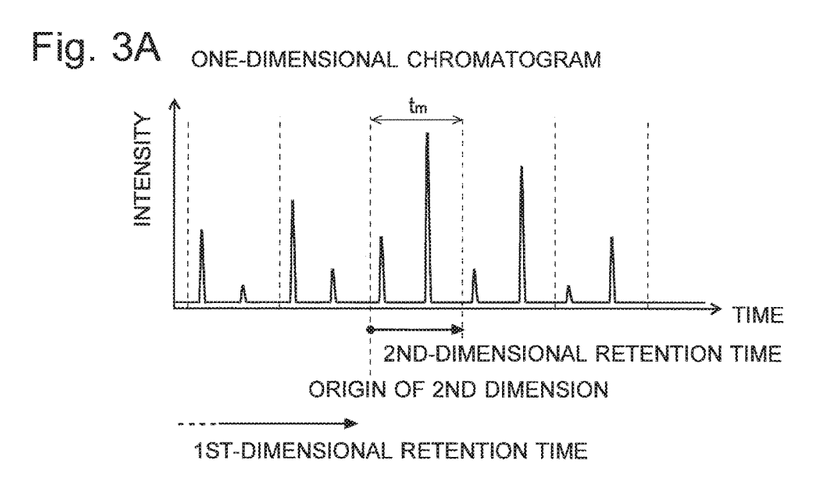
FIG. 3A is a diagram showing one example of the one-dimensional chromatogram created based on the data collected with a comprehensive two-dimensional GC.

These comprehensive two-dimensional chromatographs detect the components in a sample gas or sample solution which has passed through the two columns. Therefore, the data produced by the detector is a single sequence of data arranged in time-series order. Accordingly, by plotting the obtained data in order of generation, a one-dimensional chromatogram as shown in FIG. 3A can be created, which is similar to a chromatogram obtained with a normal GC, i.e. which has the horizontal axis indicating the retention time and the vertical axis indicating the signal intensity. In FIG. 3A, "tm" denotes the modulation time. The section of the chromatogram within this time (tm) is the chromatogram which reflects the state of separation of the components in the secondary column.

Figure 3B:
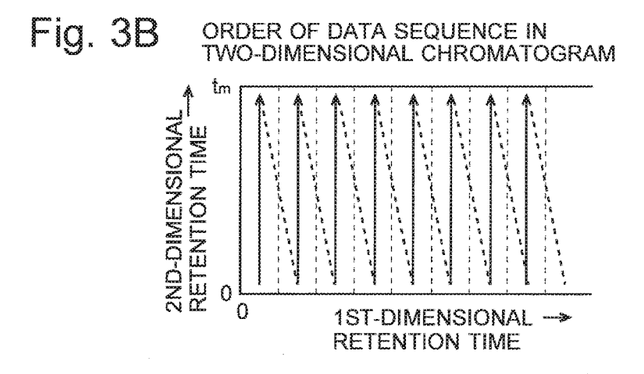
FIG. 3B is a diagram illustrating the process of creating a two-dimensional chromatogram based on a one-dimensional chromatogram.
Figure 3C:
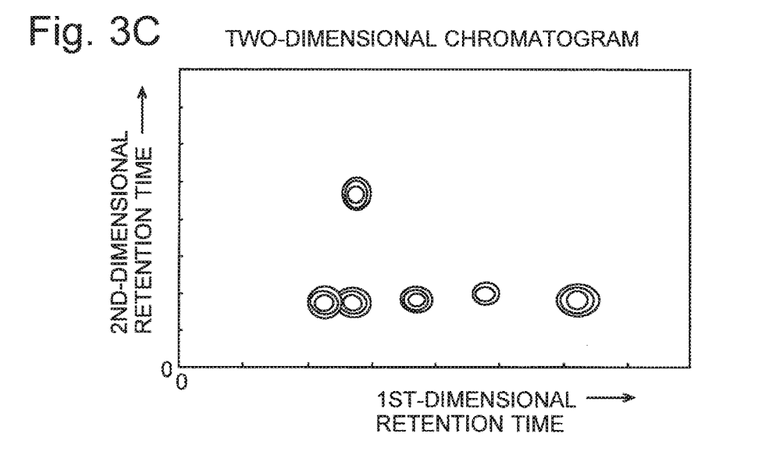
FIG. 3C is a diagram showing one example of the two-dimensional chromatogram.

As noted earlier, in many cases, the two columns in the comprehensive two-dimensional chromatograph have different separation characteristics. Therefore, to show the state of separation in each column in an easily comprehensible form, a two-dimensional chromatogram having two orthogonal axes which respectively indicate the retention time in the primary column and the retention time in the secondary column is created, with the signal intensity represented by contour lines, color scale, or gray scale. FIG. 3B illustrates the order in which the data are arrayed to create the two-dimensional chromatogram from one-dimensional chromatogram data. The range of the vertical axis of this graph corresponds to the modulation time, tm. The one-dimensional chromatogram data are sequentially plotted upward from the lower end (0) along the vertical axis (the solid arrow in FIG. 3B). After reaching tin, the plotting point is shifted rightward along the horizontal axis and returned to the lower end of the vertical axis (the broken line in FIG. 3B). After that, the upward-plotting operation along the vertical axis is once more performed. By repeating such an operation, a two-dimensional chromatogram as shown in FIG. 3C is obtained. In FIG. 3C, the signal intensity is indicated by contour lines.

In the case of a temperature-programmed analysis in which the temperature of the columns is increased with time, the horizontal axis in the two-dimensional chromatogram represents the order of the boiling point, while the vertical axis represents the order of polarity. Therefore, the analysis operator can easily understand the nature of each component on the basis of the two-dimensional chromatogram. Even when many components contained in the sample, the analysis operator can intuitively understand what kinds of components are contained.

As a data processing software product for creating such a two-dimensional chromatogram, the "GC Image" offered by GC Image LLC is commonly known.

As noted earlier, the comprehensive two-dimensional GC provides a high level of separation power, and therefore, is extremely effective for an analysis of a sample which contains a number of compounds whose retention times are close to each other, a typical example of which is a hydrocarbon analysis of diesel fuel. In particular, in such an application area, the device is commonly used in comparative analyses for various purposes, such as the discrimination of similar articles, identification of causative substances for malfunctions (or the like), or analysis of temporal changes. In order to facilitate such comparative analyses, conventional data-processing software products for comprehensive two-dimensional GCs are provided with various functions, such as the comparison of two-dimensional chromatograms, numerical comparison of the blobs detected on the two-dimensional chromatograms, as well as multivariate analysis (see Non Patent Literatures 2 and 3).

In general, the aforementioned types of comparative analyses often include the task of comparing a plurality of two-dimensional chromatograms. If there is an extremely large number of blobs on the chromatograms, the analyzing efficiency becomes low since a considerable amount of time is required for the tasks of finding a difference between the chromatograms, choosing notable blobs or compounds, and determining the correspondence between the blobs and the result of another analysis performed for the sample. No appropriate function for assisting such tasks performed by the analysis operator is provided in the conventional data-processing software products for two-dimensional GCs.

CITATION LIST

Patent Literature

Patent Literature 1: JP 2011-122822 A

Non Patent Literature

Non Patent Literature 1: Miyagawa, "Gasukuromatogu-rafi/Shitsuryoubunseki-Hou No Nouyaku Zanryuu Bunseki Eno Riyou (Sono 2)—Houkatsuteki Nijigen Gasukuro-matogurafu-Shitsuryoubunsekikei (GC×GC-MS) No Nouyaku Zanryuu Bunseki Eno Tekiyou—(Use of Gas Chromatography/Mass Spectrometry for Pesticide Residue Analysis (Part 2)—Application of Comprehensive Two-Dimensional Gas Chromatograph-Mass Spectrometer (GC× GC-MS) in Pesticide Residue Analysis)", *Japanese Journal of Pesticide Science,* 37(1), 2012, pp. 104-111

Non Patent Literature 2: S. E. Reichenbach, "Comprehensive two dimensional gas chromatography, Chapter 4: Data Acquisition, Visualization, and Analysis", Elsevier, 2009, p. 77-106

Non Patent Literature 3: "GC Image (GC×GC Edition) Users' Guide, Comparative Analysis and Visualization", [online], GC Image LLC (USA). [accessed on Jun. 9, 2014], the Internet

SUMMARY OF INVENTION

Technical Problem

The present invention has been developed in view of the previously described problem. Its objective is to provide a data processing device for a comprehensive two-dimensional chromatograph, capable of presenting analysis operators with easy-to-understand information about the blobs which should be regarded as important or notable in the task of comparing a plurality of two-dimensional chromatograms, even when there is a large number of blobs detected on the two-dimensional chromatograms. The present invention also provides a data processing device for a comprehensive two-dimensional chromatograph, capable of presenting analysis operators with compound information corresponding to a blob to be noted on a two-dimensional chromatogram with a simple operation.

Solution to Problem

The present invention developed for solving the previously described problem is a data processing device for a comprehensive two-dimensional chromatograph for processing data collected with a comprehensive two-dimensional chromatograph in which a sample separated into components by a primary column is divided at predetermined intervals of time, the divided sample is introduced into a secondary column to be further separated into components, and the components are introduced into a detector to be individually detected, the data processing device including:

a) a chromatogram creator for creating a two-dimensional chromatogram for each of two samples to be compared, based on the data collected with the comprehensive two-dimensional chromatograph for the two samples, with the two axes of the chromatogram respectively indicating the retention time in the primary column and the retention time in the secondary column;

b) a differential chromatogram creator for creating a two-dimensional differential chromatogram showing the difference in the signal intensity calculated at each corresponding temporal position between a first two-dimensional chromatogram and a second two-dimensional chromatogram created by the chromatogram creator;

c) a blob detector for detecting blobs on the first and second two-dimensional chromatograms as well as on the two-dimensional differential chromatogram according to a predetermined criterion;

d) a matching-blob extractor for conducting a comparison between the blobs detected on the two-dimensional differential chromatogram and the blobs detected on the first two-dimensional chromatogram as well as a comparison between the blobs detected on the two-dimensional differential chromatogram and the blobs detected on the second two-dimensional chromatogram, and for extracting a blob existing at the same temporal position in each of the two-dimensional chromatograms; and e) a specific blob indicator for displaying, on the first and second two-dimensional chromatograms, a blob extracted by the matching-blob extractor as the blob located at the same temporal position as a blob on the two-dimensional differential chromatogram; in such a manner that the extracted blob is distinguishable from the other blobs.

The comprehensive two-dimensional chromatograph may be either of the two types, i.e. the comprehensive two-dimensional GC and the comprehensive two-dimensional LC. As the detector for the chromatograph, any type of detector commonly used for GC and LC can be used, including mass spectrometers.

In the data processing device for a comprehensive two-dimensional chromatograph according to the present invention, for example, two samples to be subjected to a comparative analysis are specified by an analysis operator. The chromatogram creator retrieves the data collected by the comprehensive two-dimensional chromatograph for the two samples, and creates a two-dimensional chromatogram for each sample. In the two, first and second two-dimensional chromatograms created in this manner, the differential chromatogram creator calculates the difference in the signal intensity at each corresponding temporal position between the first and second chromatograms, and creates a two-dimensional differential chromatogram showing the temporal change in the difference value of the signal intensity. The blob detector detects blobs, i.e. spatial peaks, on each of the two (first and second) two-dimensional chromatograms as well as on the two-dimensional differential chromatogram according to a predetermined criterion.

It should be noted that the data value (signal-intensity value) at each temporal position in the two-dimensional differential chromatogram may possibly be a negative value. Accordingly, not only the blobs projecting in the positive direction but also those projecting in the negative direction must be detected. A blob which appears in the two-dimensional differential chromatogram indicates a temporal position where the two two-dimensional chromatograms has a significant difference in the signal intensity. It depends on the purpose of the analysis (or some other factors) what amount of difference in the signal intensity should be considered as essential, or what amount of difference in the signal intensity must be regarded as notable. Accordingly, when detecting a blob in the two-dimensional differential chromatogram, the blob detector may preferably detect a blob having an intensity whose absolute value is equal to or greater than a threshold specified by an analysis operator.

Next, the matching-blob extractor compares the blobs detected on the two-dimensional differential chromatogram and those detected on the first two-dimensional chromatogram, as well as the blobs detected on the two-dimensional differential chromatogram and those detected on the second two-dimensional chromatogram, and extracts a blob located at the same temporal position in each of the two-dimensional chromatograms. An example of the method for determining whether or not two blobs are located at the same temporal position is to set a time width for the temporal position of one of the two blobs allowing for a predetermined time margin in both the direction of the retention time in the primary column and the direction of the retention time in the secondary column, and conclude that the two blobs are located at the same temporal position if the other blob is included within that time width. It is also possible to set a time width for the retention time of a specific or arbitrary compound obtained from a database or library which contains compound information, allowing for a predetermined time margin, and conclude that the two blobs being compared are located at the same temporal position if they are both included within that time width.

A blob extracted from the first and second two-dimensional chromatograms by the matching-blob extractor as the blob which is located at the same temporal position as a blob on the two-dimensional differential chromatogram corresponds to a compound having a significant difference in the signal intensity between the two samples. In other words, it can be considered to be a blob which should be regarded as important or notable in the comparative analysis. Accordingly, when displaying the first and second two-dimensional chromatograms on a display screen, the specific blob indicator highlights this specific blob extracted in the previously described way by the matching-blob extractor so that this blob is distinguishable from the other blobs on the chromatograms. Specifically, for example, a marking in an appropriate shape for indicating the specific blob can be superposed on the chromatogram.

By this indication, the analysis operator can be informed of blobs which are useful for the comparative analysis on each of the first and second two-dimensional chromatograms.

In the data processing device for a comprehensive two-dimensional chromatograph according to the present invention, the specific blob indicator may be configured so as to display the blobs in such a manner that a blob having a positive intensity value and a blob having a negative intensity value on the two-dimensional differential chromatogram are distinguishable from each other.

As noted earlier, some blobs on a two-dimensional differential chromatogram have positive intensity values while others have negative intensity values. The previously described configuration allows the analysis operator to determine at a glance whether each specific blob is positive or negative. Accordingly, the analysis operator can intuitively understand which of the first and second two-dimensional chromatograms has a higher level of signal intensity at the temporal position of that blob.

The data processing device for a comprehensive two-dimensional chromatograph according to the present invention may preferably be configured so that: the matching-blob extractor determines whether or not the difference in the signal intensity between two extracted blobs corresponding to each other in the first and second two-dimensional chromatograms, or the ratio of that difference, is equal to or greater than a predetermined threshold if the two blobs are located at the same temporal position in the first and second two-dimensional chromatograms; and the specific blob indicator displays the blobs on the first and second two-dimensional chromatograms in such a manner that a blob equal to or greater than the predetermined threshold is distinguishable from the other blobs. Specifically, for example, the shape, color, line type or other properties of the marking may be changed to make it distinguishable.

By this configuration, the analysis operator can be informed of blobs which are even more useful for the comparative analysis in each of the first and second two-dimensional chromatograms. Needless to say, it is preferable to allow analysis operators to appropriately set the predetermined threshold used for making the judgment on the difference in the signal intensity between two blobs or on the ratio of that difference.

In the case where the data processing device for a comprehensive two-dimensional chromatograph according to the present invention is a data processing device for processing data collected with a comprehensive two-dimensional chromatograph using, as the detector, a mass spectrometer which repeatedly performs a scan measurement, the device may preferably include:

a spectrum library holding mass spectrum information linked with compound information; and a library searcher for retrieving spectrum data obtained at the temporal position at which the blob identified by the specific blob indicator is located, and for searching for the compound information corresponding to the blob by comparing a mass spectrum created from the retrieved data with mass spectra stored in the spectrum library.

That is to say, according to this configuration, the compound corresponding to the specifically located blob can be identified by a search using the spectrum library. The spectrum library is a collection of mass spectrum information linked with compound information, such as the compound name, composition formula and structural formula. For example, it may be a generally used database containing an exhaustive collection of mass spectra of commonly known compounds, such as the existing NIST database or Wiley database, it may also be a library aimed at compounds used in specific areas or for specific purposes, such as a library for agricultural chemicals, drugs or metabolites. It is preferable to additionally use the retention time for the identification of the compound.

Advantageous Effects of the Invention

The data processing device for a comprehensive two-dimensional chromatograph according to the present invention can automatically select blobs which should be regarded as important or notable for a comparative analysis, and present those blobs to analysis operators in an easily comprehensible form. With this function, analysis operators can efficiently conduct a comparative analysis using a comprehensive two-dimensional chromatograph.

DESCRIPTION OF EMBODIMENTS

Figure 1:
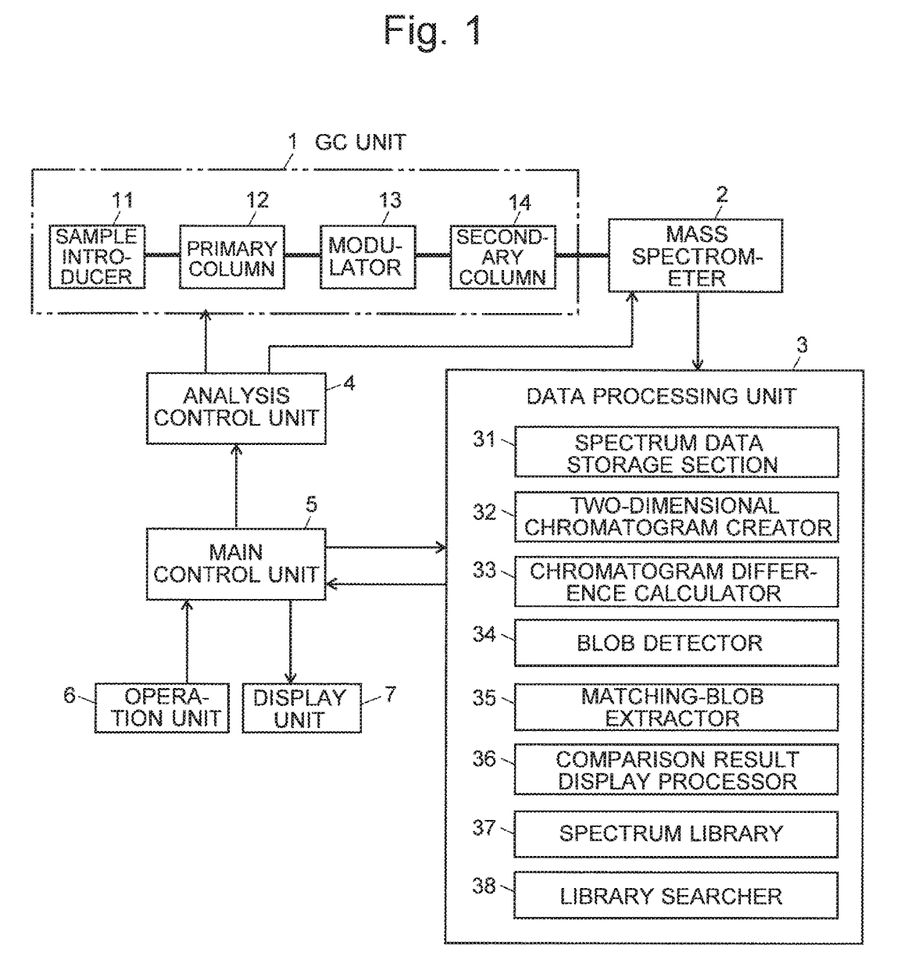
FIG. 1 is a schematic configuration diagram of one embodiment of the comprehensive two-dimensional GC-MS system equipped with a data processing device for a comprehensive two-dimensional chromatograph according to the present invention.

One embodiment of the comprehensive two-dimensional GC-MS system equipped with a data processing device for a comprehensive two-dimensional chromatograph according to the present invention is hereinafter described with reference to the attached drawings. FIG. 1 is a schematic configuration diagram of the comprehensive two-dimensional GC-MS system according to the present embodiment.

In the system of the present embodiment, a GC unit 1 includes: a primary column 12; a sample introducer 11 including a sample vaporization chamber and other elements for introducing sample gas into the primary column 12; a modulator 13 for catching components (compounds) eluted from the primary column 12 at regular intervals of time (modulation time, tin) and for sending them out in a temporally compressed form; and a secondary column 14 capable of high-speed separation with the separation characteristics different from those of the primary column 12 (typically, with a different polarity). The sample gas containing the components separated by the two-stage columns 12 and 14 is introduced into a mass spectrometer 2. The mass spectrometer 2 produces intensity signals corresponding to the amounts (concentrations) of compounds in the sample gas. For example, the mass spectrometer 2 repeatedly performs a scan measurement within a predetermined mass-to-charge-ratio range and produces mass spectrum data obtained by each scan.

The data processing unit 3 includes the following functional blocks: a data storage section 31 for collecting and storing spectrum data sequentially fed from the mass spectrometer 2 with the passage of time in the previously described manner; a two-dimensional chromatogram creator 32 for creating a two-dimensional chromatogram based on the data stored in the data storage section 31; a chromatogram difference calculator 33 for calculating the two-dimensional differential chromatogram for two two-dimensional chromatograms; a blob detector 34 for detecting a blob (two-dimensional peak) on a two-dimensional chromatogram as well as on a two-dimensional differential chromatogram; a matching-blob extractor 35 for comparing the temporal positions at which blobs appear on a plurality of chromatograms; a comparison result display processor 36 for displaying a chromatogram including the result of the matching-blob comparison; a spectrum library 37 holding mass spectrum information linked with compound information; and a library searcher 38 for identifying a compound by conducting a search using the spectrum library 37.

The operations of the GC unit 1 and mass spectrometer 2 are controlled by an analysis control unit 4. The main control unit 5, to which an operation unit 6 and display unit 7 as the user interfaces are connected, is responsible for the general control of the system. The main control unit 5, analysis control unit 4 and data processing unit 3 can be realized using a personal computer as a hardware resource by running, on that computer, a dedicated controlling and processing software program previously installed on the same computer.

Initially, the analyzing operation in the GC unit 1 and mass spectrometer 2, i.e. the operation of collecting spectrum data is schematically described.

In the GC unit 1, upon receiving a command from the analysis control unit 4, the sample introducer 11 introduces a sample to be analyzed into a carrier gas being supplied at a substantially constant flow rate. Normally, this sample contains many compounds. While passing through the primary column 12 which is temperature controlled according to a predetermined temperature-increasing program, those various compounds contained in the sample are separated, to be eluted in a temporally shifted fashion. At this point, it is not always the case that all compounds are sufficiently separated; compounds whose retention times are close to each other will be eluted in a mixed form.

The modulator 13 repeats the operation of entirely catching the compounds eluted from the primary column 12 within the modulation time, tm (which is normally a few to approximately one dozen seconds), and sending them into the secondary column 14 in a temporally compressed form with an extremely narrow bandwidth. Accordingly, the compounds eluted from the primary column 12 are sent into the secondary column 14 without omission. While passing through the secondary column 14, the compounds sent into this column at regular intervals of time defined by the modulation time, tm, are temporally separated at a high level of resolution and eluted, to be eventually introduced into the mass spectrometer 2 in order of elution. In the mass spectrometer 2, for example, all compounds can be detected without omission by performing a scan measurement at shorter intervals of time than the time width within which one compound is eluted from the secondary column 14.

The detection signals produced by the mass spectrometer 2, converted into digital data by a built-in analogue-to-digital converter (not shown) with a predetermined sampling period, and those data are outputted. The spectrum data which are sequentially obtained in this manner with the passage of time are stored in the spectrum data storage section 31. Normally, a sequence of data obtained by performing a comprehensive two-dimensional (IC-MS analysis for one sample are compiled into one data file when stored. The term "sequence of data" means a set of spectrum data repeatedly obtained from the beginning to the ending point in time of the analysis.

The comprehensive two-dimensional GC-MS system of the present embodiment is characterized by the data processing performed in a comparative analysis in which two sets of data respectively obtained for two samples in the previously described manner are compared with each other.

Figure 2:
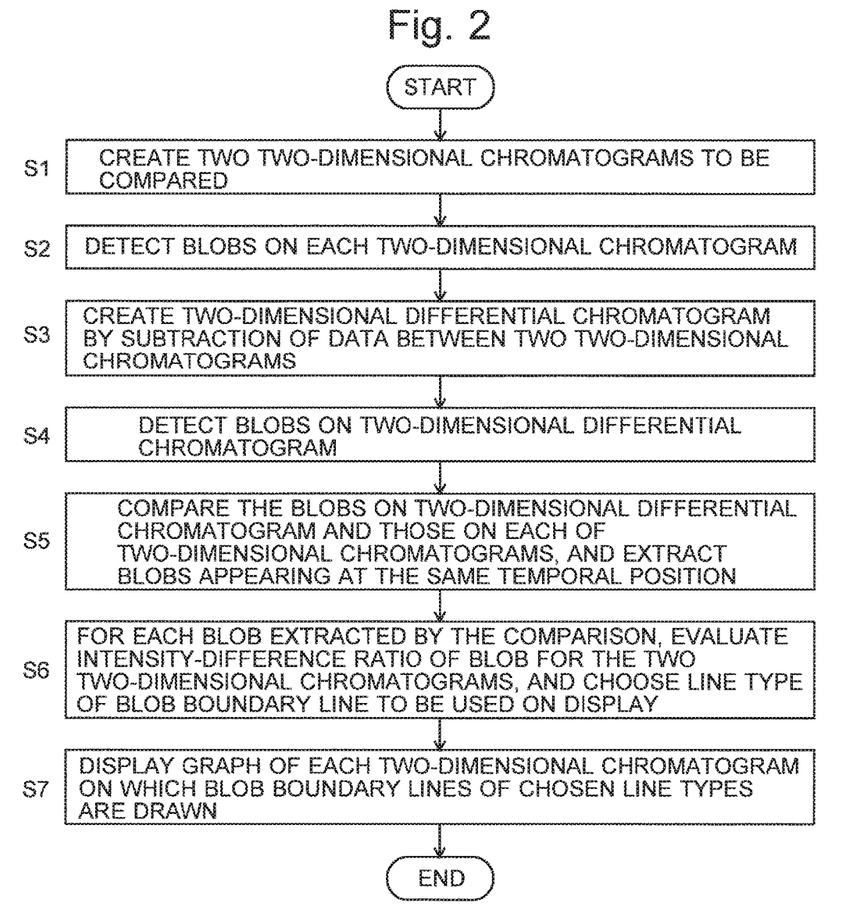
FIG. 2 is a flowchart showing a characteristic data-processing operation performed in the comprehensive two-dimensional GC-MS system according to the present invention.
Figure 4A:
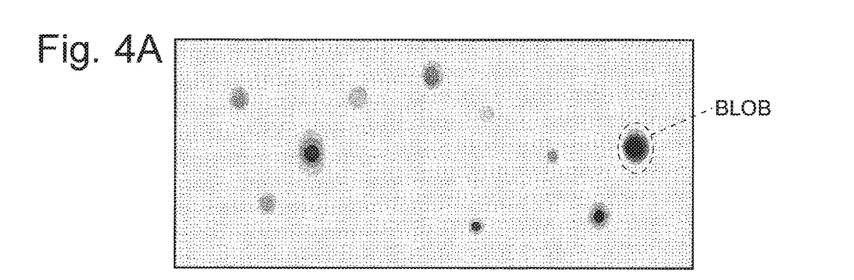
FIGS. 4A-4C are diagrams showing one example of the two-dimensional chromatograms corresponding to two samples to be compared as well as the two-dimensional differential chromatogram derived from those two-dimensional chromatograms.
Figure 4B:
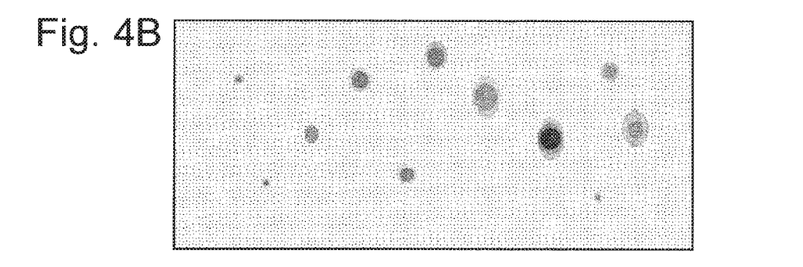
Figure 4C:
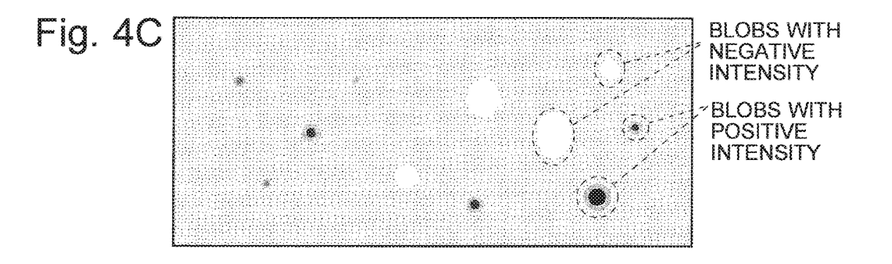
Figure 5:
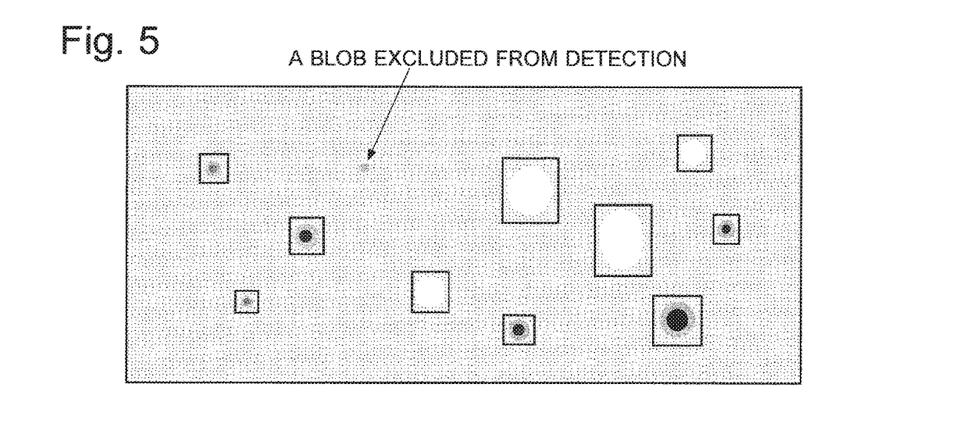
FIG. 5 is a diagram showing the result of a blob detection process performed in the two-dimensional differential chromatogram shown in FIG. 4C.
Figure 6A:
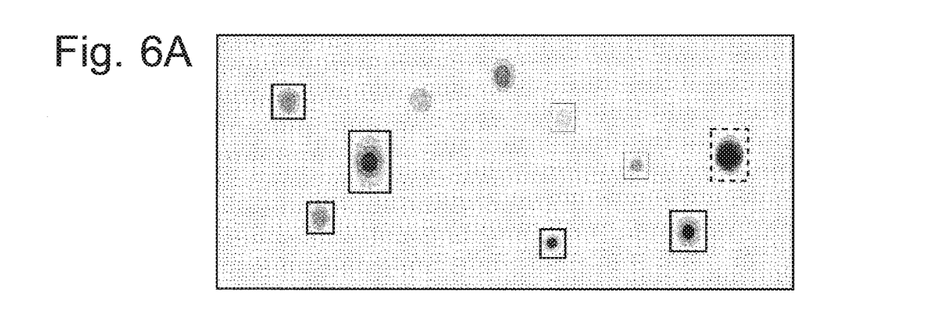
FIGS. 6A-6C are diagrams showing the result of a matching-blob comparison performed on the two-dimensional chromatograms and two-dimensional differential chromatogram shown in FIGS. 4A-4C.
Figure 6B:
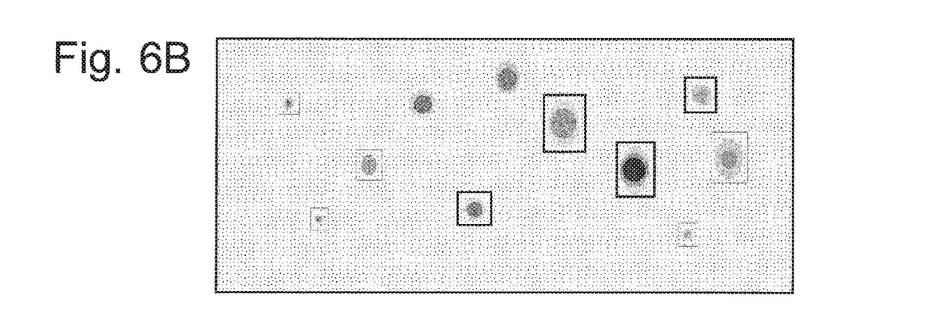
Figure 6C:
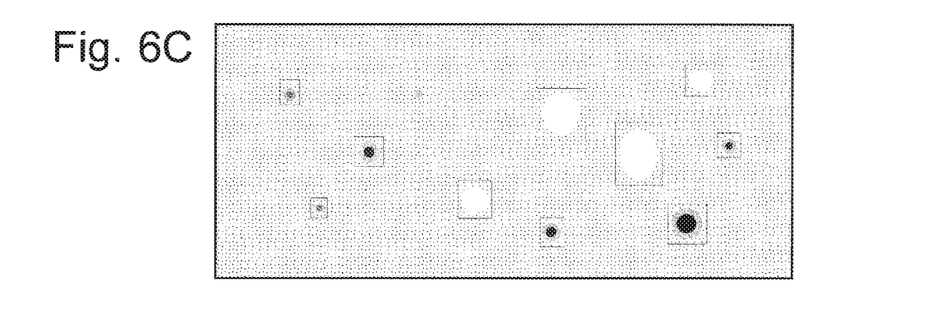

One example of this data processing is hereinafter described in detail with reference to FIG. 2 and FIGS. 4A-6C. FIG. 2 is a flowchart showing the data-processing operation. FIGS. 4A-4C are diagrams showing one example of the two-dimensional chromatograms corresponding to two samples to be compared and the two-dimensional differential chromatogram derived from those two-dimensional chromatograms. FIG. 5 is a diagram showing the result of a blob detection process performed in the two-dimensional differential chromatogram shown in FIG. 4C. FIGS. 6A-6C are diagrams showing the result of a matching-blob comparison performed on the two-dimensional chromatograms and two-dimensional differential chromatogram shown in FIGS. 4A-4C.

In the comparative analysis, the analysis operator using the operation unit 6 indicates two samples to be compared. Upon receiving this indication through the main control unit 5, the two-dimensional chromatogram creator 32 reads, from the spectrum data storage section 31, the data files corresponding to the two samples to be compared. For each mass spectrum, i.e. at each temporal position, the two-dimensional chromatogram creator 32 calculates the accumulated value of the ion intensity over a predetermined mass-to-charge-ratio range e, it calculates the chromatogram data value at one point in time), to create a two-dimensional chromatogram for each sample (Step S1). The method for creating the two-dimensional chromatogram is the same as the conventional one. For convenience, the two-dimensional chromatogram for sample A is hereinafter referred to as chromatogram "a", and the two-dimensional chromatogram for sample B as chromatogram "b". FIG. 4A is one example of chromatogram"a", while FIG. 4B is one example of chromatogram "b".

The blob detector 34 detects blobs in each of the chromatograms "a" and "b" according to a predetermined criterion (Step S2). The method for detecting a blob is also the same as the conventional one.

The chromatogram difference calculator 33 performs the process of subtracting one chromatogram "b" from the other chromatogram "a". More specifically, the calculator subtracts one data value (signal intensity value) from the other at the same temporal position in the direction of the first-dimensional retention time and the direction of the second-dimensional retention time on the two-dimensional chromatograms, and creates a two-dimensional differential chromatograms using the data values obtained by the subtraction (Step S3). It is also possible to subtract chromatogram "a" from chromatogram "b". The device may be configured so as to allow analysis operators to specify which of the two two-dimensional chromatograms should be subtracted from the other.

FIG. 4C is one example of the two-dimensional differential chromatogram obtained from chromatograms "a" and "b" shown in FIGS. 4A and 4B. In this subtracting operation, an appropriate waveform-processing operation (e.g. smoothing) used in the conventional chromatogram data processing may also be simultaneously performed. Unlike the two-dimensional chromatogram, the data values in the two-dimensional differential chromatogram are not always positive but may be negative values.

The blob detector 34 detects blobs on the two-dimensional differential chromatogram (Step S4). This blob detection process may preferably be performed using a preset threshold of the absolute value of the signal intensity at the peak position of the blob in such a manner that any blob in which the absolute value of the signal intensity at the peak position of the blob is lower than the threshold is not recognized as a blob. It is also preferable to allow analysis operators to appropriately set this threshold. By this method, low blobs which are practically useless for the comparative analysis can be excluded. FIG. 5 illustrates a chromatogram showing the result of the blob detection process performed for the two-dimensional differential chromatogram shown in FIG. 4C. The blobs surrounded by the rectangular boundary lines in the figure are the detected blobs.

In a two-dimensional differential chromatogram, the value of the signal intensity at the peak of the blob may be positive at some blobs and negative at the other. It is preferable to make those blobs easy to be visually distinguished. Accordingly, in FIG. 5, blobs having negative signal-intensity values at their peaks are shown in white, while those having positive signal-intensity values at their peaks are shown in black or gray.

Next, the matching-blob extractor 35 compares the temporal position of the blobs detected on the two-dimensional differential chromatogram and that of the blobs detected on chromatogram "a", as well as the temporal position of the blobs detected on the two-dimensional differential chromatogram and that of the blobs detected on chromatogram "b", to extract mutually corresponding blobs (Step S5). Specifically, for example, a time width is set around the temporal position of the peak of one blob detected on the two-dimensional differential chromatogram, allowing for a predetermined amount of margin before and after that temporal position. If a blob detected on chromatogram "a" or one detected on chromatogram "b" is located within that time width, it is concluded that the blob detected on the two-dimensional differential chromatogram corresponds to the blob located on chromatogram "a" or "h". For one blob detected on the two-dimensional differential chromatogram, the corresponding blobs may be located on both chromatograms "a" and "b", or one corresponding blob may be located on only one of the chromatograms "a" and "b".

If the corresponding blobs have been located on both chromatograms "a" and "b", the matching-blob extractor 35 calculates the intensity ratio of the difference between the intensity of the blob detected on chromatogram "a" and that of the blob detected on chromatogram "h". In other words, it calculates the intensity-difference ratio α, which is defined by the following equation:

$$\alpha[\%]=[\{I(A)-I(B)\}/I(A)]\times 100$$

where I(A) is the intensity of a blob on chromatogram "a", and I(B) is the intensity of the corresponding blob on chromatogram "b". This intensity-difference ratio α can be considered to be a normalized intensity difference which enables a comparison of the intensity values among different blobs.

After the calculation of the intensity-difference ratio α has been completed for all corresponding blobs on the two chromatograms "a" and "h", the line type of the blob boundary line (which will be described later) is determined according to the intensity-difference ratio α (Step S6). In the present example, the line type is chosen by the following decision rules (i), (ii), (iii) and (iv) with R[%] representing the threshold of the intensity previously specified by the analysis operator:

(i) If the intensity-difference ratio α is positive and |α|≥R, a thick solid line is chosen as the boundary line of the blob on chromatogram"a", while a thin solid line is chosen as the boundary line of the blob on chromatogram "b".

(ii) If the intensity-difference ratio α is positive and |α|<R, a thick broken line is chosen as the boundary line of the blob on chromatogram "a", while a thin broken line is chosen as the boundary line of the blob on chromatogram "b".

(iii) If the intensity-difference ratio α is negative and $|\alpha| \geq R$, the thick solid line is chosen as the boundary line of the blob on chromatogram "b", while the thin solid line is chosen as the boundary line of the blob on chromatogram "a".

(iv) If the intensity-difference ratio α is negative and $|\alpha| < R$, the thick broken line is chosen as the boundary line of the blob on chromatogram "b", while the thin broken line is chosen as the boundary line of the blob on chromatogram "a".

Needless to say, the operation of choosing the boundary line is omitted if the blob concerned on the two-dimensional differential chromatogram has only one corresponding blob located on either chromatogram "a" or "b".

The comparison result display processor 36 displays, on the screen of the display unit 7, a chromatogram in which each of the blobs extracted on the chromatograms "a" and "h" in Step S5 is surrounded by a rectangular boundary line drawn with the line type chosen in Step S6 (Step S7). As a result, for example, chromatograms as shown in FIGS. 6A and 6B are displayed. On these chromatograms, one can at a glance locate the blobs which have the intensity-difference ratios equal to or higher than the threshold and therefore should be considered as important in the comparative analysis. As for the two-dimensional differential chromatogram, all blobs extracted in Step S5 are individually surrounded by the boundary line of the same line type when the chromatogram is displayed on the screen of the display unit 7. As a result, for example, a chromatogram as shown in FIG. 6C is displayed.

By the processes described to this point, the comprehensive two-dimensional GC-MS system of the present embodiment can present the analysis operator with the blobs which are important for the comparative analysis. Additionally, the system can also provide the analysis operator with information about the compound corresponding to a blob which has been judged to have a significant intensity-difference ratio, as will be hereinafter described.

After the chromatograms as described earlier are displayed, if the analysis operator using the operation unit 6 performs a specific operation (or if the device is appropriately configured beforehand), the library searcher 38 obtains information on the temporal position of the peak of a blob extracted on one or both of the chromatograms "a" and "h". Then, it reads, from the spectrum data storage section 32, a set of mass spectrum data obtained at that temporal position and creates the mass spectrum. Subsequently, the library searcher 38 compares the spectrum pattern of that mass spectrum with those of the mass spectra held in the spectrum library 37, to search for a compound which has a highly similar mass spectrum.

If one compound has been located with a high degree of certainty by the search, that compound is obtained as the search result. If a plurality of compounds have been located and they cannot be narrowed to one, those compound candidates are obtained as the search result along with the scores indicating their degrees of certainty. The obtained information, such as the compound name, is presented to the analysis operator by being superposed on the chromatograms or listed in a table apart from the chromatograms. With this information, the analysis operator can identify the compound which has a significant intensity difference in the comparative analysis. It is also possible to verify the appropriateness of the matching-blob comparison by determining whether or not the compound identified for the blob on chromatogram "a" is the same as the one identified for the blob on chromatogram "b".

If the compound information held in the spectrum library 37 contains the retention time, the retention time can additionally be used for the identification of the compound. That is to say, if the temporal position at which a blob appears corresponds to the retention time of a certain compound X, and if the mass spectrum obtained at that temporal position shows a high degree of matching with the spectrum pattern of the mass spectrum of compound X, the compound corresponding to the blob can be identified as compound X.

It should be noted that the previous embodiment is a mere example of the present invention, and any change, modification or addition appropriately made within the spirit of the present invention will evidently fall within the scope of claims of the present application.

For example, the data processing device for a comprehensive two-dimensional chromatograph according to the present invention can be applied in not only the processing of data obtained with a comprehensive two-dimensional GC-MS or comprehensive two-dimensional GC, but also in the processing of data obtained with a comprehensive two-dimensional LC-MS or comprehensive two-dimensional LC.

REFERENCE SIGNS LIST

1 . . . GC Unit
11 . . . Sample Introducer
12 . . . Primary Column
13 . . . Modulator
14 . . . Secondary Column
2 . . . Mass Spectrometer
3 . . . Data Processing Unit
31 . . . Spectrum Data Storage Section
32 . . . Two-Dimensional Chromatogram Creator
33 . . . Chromatogram Difference Calculator
34 . . . Blob Detector
35 . . . Matching-Blob Extractor
36 . . . Comparison Result Display Processor
37 . . . Spectrum Library
38 . . . Library Searcher
4 . . . Analysis Control Unit
5 . . . Main Control Unit
6 . . . Operation Unit
7 . . . Display Unit

The invention claimed is:

1. A data processing device for a comprehensive two-dimensional chromatograph for processing data collected with a comprehensive two-dimensional chromatograph in which a sample separated into components by a primary column is divided at predetermined intervals of time, the divided sample is introduced into a secondary column to be further separated into components, and the components are introduced into a detector to be individually detected, the data processing device comprising:

a) a chromatogram creator for creating a two-dimensional chromatogram for each of two samples to be compared, based on the data collected with the comprehensive two-dimensional chromatograph for the two samples, with two axes of the chromatogram respectively indicating a retention time in the primary column and a retention time in the secondary column;

b) a differential chromatogram creator for creating a two-dimensional differential chromatogram by calculating a difference in a signal intensity calculated at each corresponding temporal position between a first two-dimensional chromatogram and a second two-dimensional chromatogram created by the chromatogram creator;
c) a blob detector for detecting blobs on the first and second two-dimensional chromatograms as well as on the two-dimensional differential chromatogram according to a predetermined criterion;
d) a matching-blob extractor for conducting a comparison between the blobs detected on the two-dimensional differential chromatogram and the blobs detected on the first two-dimensional chromatogram as well as a comparison between the blobs detected on the two-dimensional differential chromatogram and the blobs detected on the second two-dimensional chromatogram, for extracting a blob existing at the same temporal position in each of the two-dimensional chromatograms, and for calculating a ratio of the difference in signal intensity; and
e) a specific blob indicator for displaying, on the first and second two-dimensional chromatograms, a blob extracted by the matching-blob extractor as the blob located at the same temporal position as a blob on the two-dimensional differential chromatogram based on the ratio of the difference in signal intensity, in such a manner that the extracted blob is distinguishable from other blobs,
wherein $\alpha\ [\%]=[\{I(A)-I(B)\}/I(A)]\times 100$,
wherein $\alpha$ is the ratio of the difference, $I(A)$ is an intensity of a blob on the first two-dimensional chromatogram, and $I(B)$ is an intensity of a corresponding blob on the second two-dimensional chromatogram.

2. The data processing device for a comprehensive two-dimensional chromatograph according to claim 1, wherein:
the specific blob indicator displays the blobs in such a manner that a blob having a positive intensity value and a blob having a negative intensity value on the two-dimensional differential chromatogram are distinguishable from each other.

3. The data processing device for a comprehensive two-dimensional chromatograph according to claim 1, wherein:
the matching-blob extractor determines whether or not the difference in the signal intensity between two extracted blobs corresponding to each other in the first and second two-dimensional chromatograms, or the ratio of the difference, is equal to or greater than a predetermined threshold if the two blobs are located at the same temporal position in the first and second two-dimensional chromatograms; and the specific blob indicator displays the blobs on the first and second two-dimensional chromatograms in such a manner that a blob equal to or greater than the predetermined threshold is distinguishable from the other blobs.

4. The data processing device for a comprehensive two-dimensional chromatograph according to claim 1, for processing data collected with a comprehensive two-dimensional chromatograph using, as a detector, a mass spectrometer which repeatedly performs a scan measurement, the data processing device further comprising:
a spectrum library holding mass spectrum information linked with compound information; and
a library searcher for retrieving spectrum data obtained at the temporal position at which the blob identified by the specific blob indicator is located, and for searching for the compound information corresponding to the blob by comparing a mass spectrum created from the retrieved data with mass spectra stored in the spectrum library.

5. The data processing device for a comprehensive two-dimensional chromatograph according to claim 2, wherein:
the matching-blob extractor determines whether or not the difference in the signal intensity between two extracted blobs corresponding to each other in the first and second two-dimensional chromatograms, or the ratio of the difference, is equal to or greater than a predetermined threshold if the two blobs are located at the same temporal position in the first and second two-dimensional chromatograms; and the specific blob indicator displays the blobs on the first and second two-dimensional chromatograms in such a manner that a blob equal to or greater than the predetermined threshold is distinguishable from the other blobs.

6. The data processing device for a comprehensive two-dimensional chromatograph according to claim 2, for processing data collected with a comprehensive two-dimensional chromatograph using, as a detector, a mass spectrometer which repeatedly performs a scan measurement, the data processing device further comprising:
a spectrum library holding mass spectrum information linked with compound information; and
a library searcher for retrieving spectrum data obtained at the temporal position at which the blob identified by the specific blob indicator is located, and for searching for the compound information corresponding to the blob by comparing a mass spectrum created from the retrieved data with mass spectra stored in the spectrum library.

7. The data processing device for a comprehensive two-dimensional chromatograph according to claim 3, for processing data collected with a comprehensive two-dimensional chromatograph using, as a detector, a mass spectrometer which repeatedly performs a scan measurement, the data processing device further comprising:
a spectrum library holding mass spectrum information linked with compound information; and
a library searcher for retrieving spectrum data obtained at the temporal position at which the blob identified by the specific blob indicator is located, and for searching for the compound information corresponding to the blob by comparing a mass spectrum created from the retrieved data with mass spectra stored in the spectrum library.

8. The data processing device for a comprehensive two-dimensional chromatograph according to claim 5, for processing data collected with a comprehensive two-dimensional chromatograph using, as a detector, a mass spectrometer which repeatedly performs a scan measurement, the data processing device further comprising:
a spectrum library holding mass spectrum information linked with compound information; and
a library searcher for retrieving spectrum data obtained at the temporal position at which the blob identified by the specific blob indicator is located, and for searching for the compound information corresponding to the blob by comparing a mass spectrum created from the retrieved data with mass spectra stored in the spectrum library.

* * * * *